United States Patent
Rauscher et al.

(10) Patent No.: US 6,887,277 B2
(45) Date of Patent: May 3, 2005

(54) SHOULDER JOINT PROSTHESIS

(75) Inventors: Markus Rauscher, Allenwinden (CH); Peter Wendt, Wiesendangen (CH)

(73) Assignee: Centerpulse Orthopedics Ltd., Baar (CH)

( * ) Notice: Subject to any disclaimer, the term of this patent is extended or adjusted under 35 U.S.C. 154(b) by 0 days.

(21) Appl. No.: 10/287,289

(22) Filed: Nov. 4, 2002

(65) Prior Publication Data
US 2003/0097183 A1 May 22, 2003

(30) Foreign Application Priority Data

Nov. 21, 2001 (EP) .............................................. 01811120
Aug. 21, 2002 (EP) .............................................. 02018730

(51) Int. Cl.$^7$ .................................................. A61F 2/40
(52) U.S. Cl. .................................................. 623/19.13
(58) Field of Search .......................... 623/18.11, 19.11, 623/19.12, 19.13, 19.14, 23.39, 23.4, 23.42, 23.43, 23.44, 23.46, 23.35

(56) References Cited

U.S. PATENT DOCUMENTS

| 4,003,095 | A | | 1/1977 | Gristina |
| 4,738,681 | A | * | 4/1988 | Koeneman et al. ............ 623/23 |
| 4,964,865 | A | * | 10/1990 | Burkhead et al. ............. 623/19 |
| 5,156,626 | A | * | 10/1992 | Broderick et al. ............ 623/22 |
| 5,489,310 | A | * | 2/1996 | Mikhail ........................ 623/19 |
| 5,507,819 | A | * | 4/1996 | Wolf ........................... 623/19 |
| 5,569,263 | A | | 10/1996 | Hein |
| 5,702,457 | A | * | 12/1997 | Walch et al. ................. 623/19 |
| 5,741,335 | A | | 4/1998 | Gerber et al. |
| 5,885,295 | A | | 3/1999 | McDaniel et al. |
| 6,197,062 | B1 | * | 3/2001 | Fenlin ...................... 623/19.12 |
| 6,197,063 | B1 | | 3/2001 | Dews |
| 6,508,840 | B1 | * | 1/2003 | Rockwood, Jr. et al. . 623/19.12 |
| 2001/0011193 | A1 | * | 8/2001 | Nogarin ................. 623/19.14 |
| 2002/0116068 | A1 | * | 8/2002 | McLean .................. 623/22.15 |
| 2003/0028253 | A1 | * | 2/2003 | Stone et al. ............. 623/19.14 |

FOREIGN PATENT DOCUMENTS

| EP | 0 679 375 A | 11/1995 | |
| EP | 0 931 522 A1 | 7/1999 | |
| EP | 0 953 321 A | 11/1999 | |
| EP | 1 314 407 A1 | 5/2003 | |
| EP | 1 321 114 A1 | 6/2003 | |
| FR | 2706283 | * 12/1994 | ............. A61F/2/32 |
| FR | 2721200 | * 12/1995 | ............. A61F/2/36 |
| FR | 2 727 857 | 6/1996 | |
| WO | WO 97 25943 A | 7/1997 | |
| WO | WO 99/37254 | 7/1999 | |

* cited by examiner

Primary Examiner—Eduardo C. Robert
Assistant Examiner—Anuradha Ramana
(74) Attorney, Agent, or Firm—Christie, Parker & Hale, LLP

(57) ABSTRACT

A shoulder joint prosthesis is shown having two bearing bodies (1, 2; 11, 12) which slide on one another and which can be respectively connected to the upper arm (3) by a shaft (5) and to the shoulder bone (4) by a platform (6). When the connection to the shaft (5) is brought about by a non-rotationally symmetrical, conical body (7) with a self-locking seat, with its periphery (8) being form matched to a mating shape (15) in the shaft (5) which is rotationally fixed relative to a longitudinal axis (9) arid keyed by the taper so that the connection is releasable and repeatedly fixable in the same angular position, large forces can be transmitted by the connection.

9 Claims, 4 Drawing Sheets

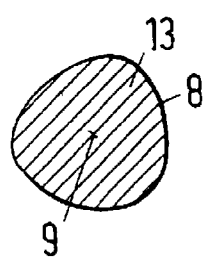
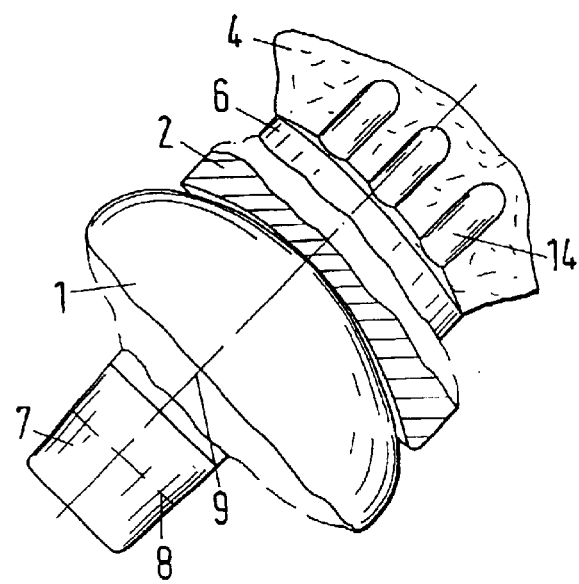
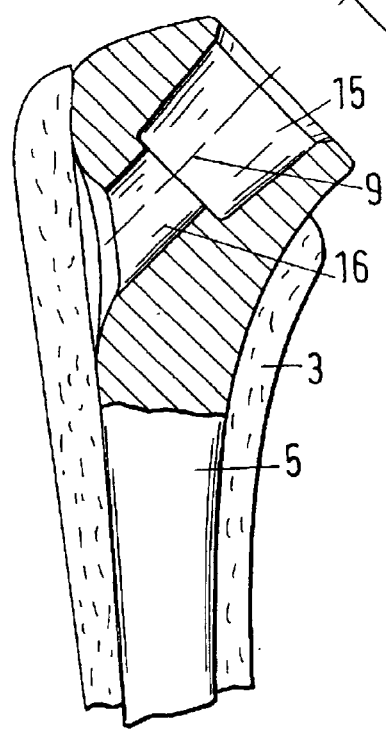
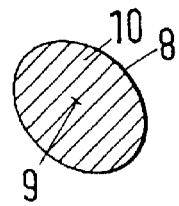

SHOULDER JOINT PROSTHESIS

CROSS-REFERENCE TO RELATED APPLICATIONS

This application claims priority of European Patent Application Nos. 01 811 120.3, filed on Nov. 21, 2001 and 02 018 730.8, filed on Aug. 21, 2002.

FIELD OF THE INVENTION

The invention relates to a shoulder joint prosthesis having two bearing bodies which slide on one another and which can be respectively connected to the upper arm by a shaft and to the shoulder bone by a platform.

BACKGROUND OF THE INVENTION

A prosthesis of this kind is shown in the patent application WO 97/25943. A bearing body connectable to a shaft in the upper arm has, at its lower side, a projecting cone with a circular cross-section and index bores for a pin projecting out of the shaft to fix the bearing body with its circular cone in different angular positions. With this arrangement, the index bores and the projecting pin must have a minimum clearance relative to one another so that the cone and the counter surface reliably form a connection. Due to this clearance, torsional forces are also transmitted at the connection which can only be transmitted by the static friction and which occur in addition to the axial loads at the friction points. Such a frictional connection is more at risk as a connection by the additionally occurring shear stresses through torsional loading, with a spread of the transmittable forces already arising from the blow by which a press-fit has to be produced and from the condition at the cone surfaces.

SUMMARY OF THE INVENTION

It is therefore the object of the present invention to provide a better connection for an attachment to the shaft of a shoulder joint prosthesis. This object is satisfied by the characterising features of independent claims 1 and 9 in that the connection to the shaft is brought about by a non-rotationally symmetrical, conical body with a self-locking seat, with its periphery being form matched to a mating shape in the shaft (5) which is rotationally fixed relative to a longitudinal axis and keyed by the amount of taper so that the connection is releasable and repeatedly fixable in the same angular position.

Such an arrangement has the advantage that components of normal forces are already present relative to the longitudinal axis of the connection in both directions of rotation due to the strain in the state of rest and, with a torsional stress, can act in opposition in accordance with the distance of their line of action from the axis of rotation. A further advantage consists in the fact that contact points can be deliberately chosen through the deviation from the circular cross-section of the cone connection which do not undergo any dilation at the outer conical sleeve dependent only on the ring tension and the elasticity of the material, but rather produce an additional bending load at the sleeve, which corresponds to a softer spring effect of the sleeve and thus produces a greater pushing on path and more reliability for an achieved holding force.

Further advantageous developments of the invention result from dependent claims 2 to 8. Thus, it is advantageous, with an elliptical periphery of the conical body, to select the desired contact points such that their radial distance from the longitudinal axis lies between the magnitude of the major and minor semi-axes of the ellipse, but closer to that of the major semi-axis. The situation is similar with a body having an outline formed by three curves and of constant diameter in which the contact points should lie with their radial distance to the longitudinal axis between the magnitude of the smallest and the largest arch spacing, but closer to that of the largest arch spacing. Generally contact points are good in which the line of action of the normal force has a large perpendicular distance from the longitudinal axis.

The strength of the conical connection, which is repeatedly detachable, also allows a conical body with a spherical cup to be attached to an already implanted shaft in a modification with respect to the natural shoulder joint, the spherical cup being pivotally mounted on a spherical head attached to the platform. This reversal of the joint, which allows less sliding and mainly a pivoting about the centre of the ball, is necessary when the ligaments are seriously damaged. The strength of the conical connection also allows more complex applications to be included such as are shown in the patent application FR 2727857 A1. In this publication, embodiments are shown with a shaft which ends as a longitudinally slit ball with a conical bore in order to fix the ball in a spherical recess of the bearing head via a conical pressure body. Since this ball is moulded onto the conical body of the present invention and this also receives an adjusting screw and the conical pressure body, the shaft can be initially implanted, then the best angular position of the bearing head can be fixed with a manipulating prosthesis placed on as a conical body and the same angular position can be set at a bearing head of the same size independent of the already implanted shaft. Such an angular position can additionally be secured by a pin projecting from the conical body and engaging in a matching bore in the spherical mount of the bearing head.

A further possibility for the fixing of the spherical joint in the bearing body consists of an oppositely slit spherical body with a conical bore which can be placed onto an additional circular cone which is formed on the conical body and which can be fixed in the bearing body by a blow on the mounted bearing body and can be retained by self-locking by friction at the conical body.

A further improvement of the conical connection between the conical body and the mating shape in the shaft is achieved when the contact points are distributed in two planes standing transversely to the longitudinal axis and when the two planes have a pre-set minimum distance from one another. This is achieved, for example, by an interruption of the engagement surface in the central region of the conical body.

BRIEF DESCRIPTION OF THE DRAWINGS

The invention will be described in the following with reference to embodiments. There are shown:

FIG. 1: schematically, a shaft implanted in the humerus;

FIG. 2: schematically, an artificial shoulder joint with a bearing head which has a conical body matching the shaft of FIG. 1;

FIG. 3: schematically, a cross-section through a conical body in accordance with FIG. 2 with an elliptically extending periphery;

FIG. 4: schematically, a cross-section through a conical body in accordance with FIG. 2 in which the periphery corresponds to a body having an outline formed by three curves and of constant diameter;

DETAILED DESCRIPTION

Figure 5:
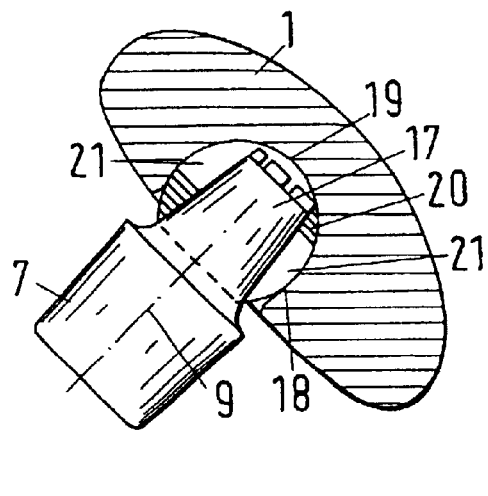
FIG. 5: schematically, in section, a bearing body which can be connected via a fixable spherical joint to a conical body in accordance with FIG. 2 by a blow.

In the following embodiments, the same reference symbols are used for the same functions.

A first embodiment is shown in FIGS. 1 and 2. A shaft 5 is implanted in a humerus 3, with the shaft 5 being anchored directly in a prepared bone bed. The shaft can, however, equally well be a shaft anchored in the humerus with bone cement. A bore 16 is provided in the direction of a longitudinal axis 9 for the actual shoulder joint and ends in a mating shape 15 for a conical body 7. The actual joint is formed by a bearing head 1 rigidly connected to the conical body 7 and by a bearing shell 2 which is in turn rigidly connected to a platform 6 anchored in the shoulder bone 4. Spigots 14 are provided parallel to one another at the platform 6 to anchor the platform 6 and are anchored in prepared bores of the shoulder bone 4, for example, with bone cement or by a press fit.

The conical body 7 and, accordingly, the mating shape 15 have a cross-section 10 with a periphery 8 which, in accordance with FIG. 3, is elliptical in shape. A cross-section derived from an equilateral triangle is shown in FIG. 4 which corresponds to a body having an outline formed by three curves and of constant diameter 13, a shape which is used as a connection between two shafts in mechanical engineering.

Figure 12:
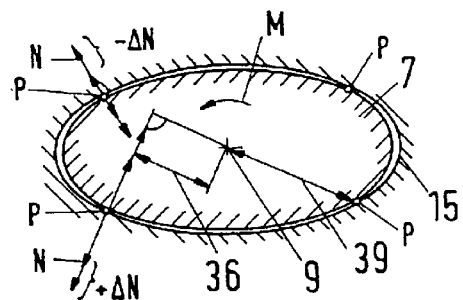
FIG. 12: schematically, a section in accordance with FIG. 3, at which a rotationally fixed keying is shown between the conical body and the mating shape.
Figure 13:
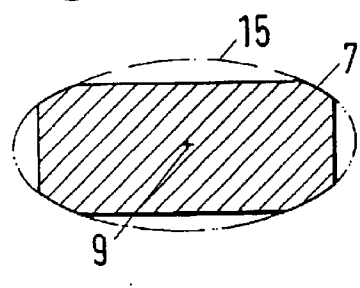
FIG. 13: schematically, a section through a conical body with an originally rectangular cross-section at the subsequently conical part areas which were made elliptical in section and matched to a mating shape in accordance with FIG. 12.

The relationships aimed at for an approximately elliptical cross-section are shown in FIG. 12. Four contact points P, which expand to form contact areas on intensive pressing, are provided by slight deviations in shape between the conical body 7 and the mating shape 15. A radial spacing 39 of a contact point P is selected such that the line of action of a pressure load N passes the longitudinal axis 9 at a relatively large spacing 36 to transmit components of a torque M as changes of normal forces. A torque M additionally engaging at the conic body 7 is thus compensated by reduction in the pre-stress or respectively by an increase of the pre-stress N by a fraction ΔN. The pre-stressed local shape match is thus decisive. The same situation is shown more extremely in FIG. 13. The conical body 7 is now only in contact with the elliptical base shape 15 in the region of the contact point expanded to form contact areas. The remaining areas are set back.

Figure 14:
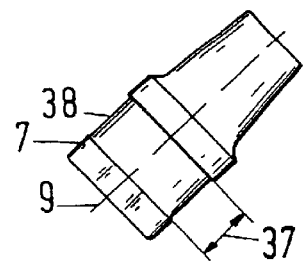
FIG. 14: schematically, a conical body in accordance with FIG. 6, in which an interruption is worked into the central region of the conical area.

A further possibility for the modification of the conical body 7 is shown in FIG. 14. To be able to transmit the largest possible bending moments in the longitudinal axis 9, the tensioning takes place in two cross-sections or raised surfaces which lie apart by a minimum spacing 37. This means that the cone has an interruption or depression 38 of this minimum spacing 37 in the central region.

With a body having an outline formed by three curves and of constant diameter, such as is shown in FIG. 4, more than three contact points are likewise aimed at within the frame of the production tolerances, with the lines of action of the normal forces of some contact points being likewise intended to lie at a distance from the longitudinal axis 9.

Figure 6:
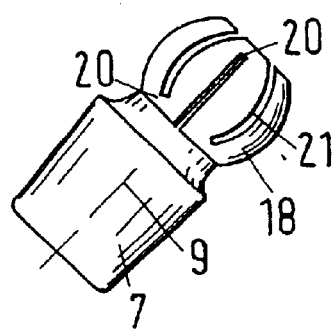
FIG. 6: schematically, a view of a spherical body and the conical body of FIG. 5.

In the example of FIGS. 5 and 6, the rigid connection between the conical body 7 and the bearing head 1 are realised by a fixable ball joint. The bearing head has a spherical recess 19 which includes an angle of more than 180° in the longitudinal section. A compressible spherical body 18 can be inserted into this recess 19. Said body is compressible because it has a continuous inner bore and slits 21 which are provided at alternate sides and which leave narrow bridges 20 standing at the end faces. Since the inner bore is designed as a circular cone, the spherical body 18 can be spread apart by a matching circular cone 17 formed on the conical body 7. The cone angle of this circle cone 17 is selected to be self locking, which has the result that, after a blow onto the bearing head 1 or onto the conical body 7 in the direction of the longitudinal axis 9, the bearing head 1 is fixed relative to the spherical body 18 and the spherical body 18 is fixed relative to the conical body 7.

Figure 7:
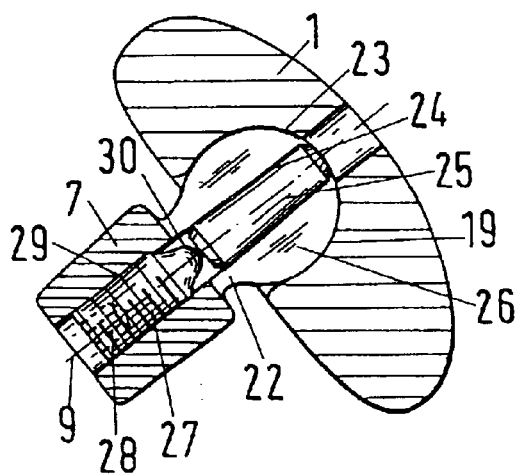
FIG. 7: schematically, in section, a bearing body in which a spherical joint can be fixed between the bearing body and a conical body by a screw extending in the axial direction of the conical body.
Figure 10:
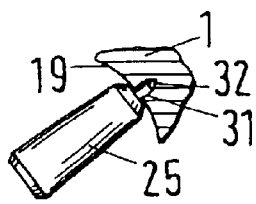
FIG. 10: schematically, a section of FIG. 7 with a pressure body which has a pin-shaped projection for an additional securing in the bearing body.
Figure 11:
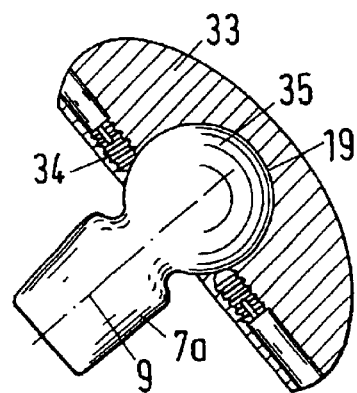
FIG. 11: schematically, a trial bearing head for an arrangement in accordance with FIG. 7.

A further example for a fixable ball joint between the bearing head 1 and the conical body 7 is shown in FIG. 7. A neck 22 and a ball 23 are formed on the conical body 7. The ball 23 has a conical bore 24 and elongate slits which extend from the apex up to and into the neck 22 so that the neck 22 is divided into a plurality of bending elements. As long as the conical bore 24 is empty, the ball 23 can be compressed and inserted into the spherical recess 19 of the bearing head 1. Only when a conical pressure body 25 is inserted through a tapped bore 29 in the conical body 7 and is driven forward by a screw 27, can the segments of the ball 23 separated by elongate slits 26 be spread apart, with the neck area forming a kind of flexural spring and yielding joint. Instead of the screw 27, a ram can also be inserted to fix the conical pressure body 25 by a blow to the ram. The screw 27 is a grub screw provided with a hexagonal socket 28 and drives the conical pressure body 25 forwards with a nose 30. Since plastic deformations can also occur due to the short dimensions in the neck region, only a one-time setting procedure is provided. For this purpose, in accordance with FIG. 11, a conical body 7a and a trial bearing head 33, which have the same construction externally, are inserted in the shaft 5 (FIGS. 1 and 2) to find an optimum position for the trial bearing head 33. The conical body 7a has a rigid ball head 35 on which grub screws 34 engage to fix the trial bearing head 33 in its optimum position. Subsequently, the conical body 7a and the trial bearing head 33 are released from the shaft 5 to copy the position of the trial bearing head 33 relative to the conical body 7a on the final conical body 7 and its bearing head 1 (FIG. 7) outside the operating field. A way of realising a copying procedure of this kind for achieving the same relative position can appear is shown in the patent application EP-A-0 931 522; however, only the conical body 7, 7a releasable from the shaft has to be clamped in the same apparatus. In accordance with FIG. 10, in the optimum position, a recess 32 can be provided in the spherical recess 19 of the bearing head into which a pin-shaped projection 31 of the conical pressure body 2 projects as an additional security against rotation.

Figure 9:
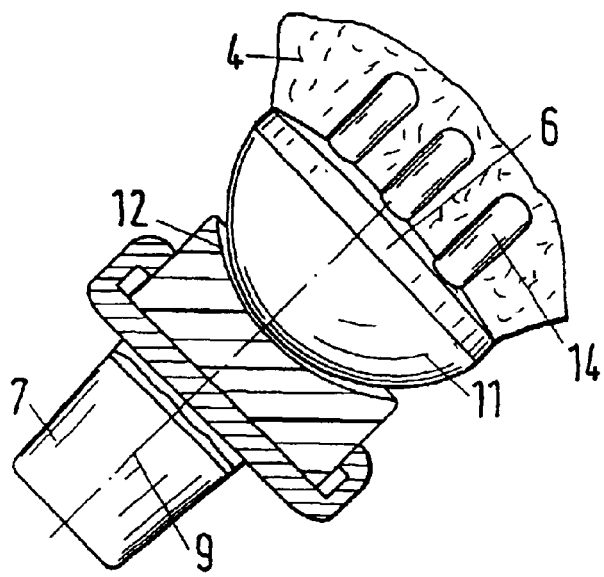
FIG. 9: schematically, a conical body which matches the shaft of FIG. 8 and which, with a spherical cup, forms an artificial shoulder joint to a spherical head which is secured via a platform to the shoulder bone.
Figure 8:
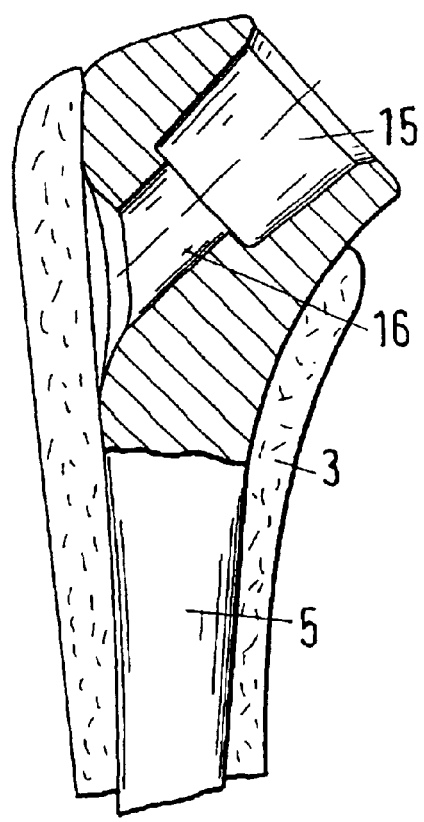
FIG. 8: schematically, a shaft implanted in a humerus with a mating shape for a conical body.

In the example of FIGS. 8 and 9, the functions of the ball and the bearing shell are exchanged, in order to allow the upper arm to rotate about a point of rotation. The shaft 5 implanted in the upper arm 3 is in turn provided with a bore 16 and a mating shape 15 for a conical body 7. The conical body 7 is, however, broadened to form a mount for a ball shell 12 which in turn partly surrounds a ball head 11. The ball head is secured to a platform 6, which is anchored in the shoulder bone 4 via spigots 14, by a snap connection or screw connection (neither being shown here). The anchoring of the platform 6 can equally take place via bone screws and projecting ribs in the shoulder bone.

In FIG. 14, a conical body 7 is shown in which the carrying conical part has an interruption 38. In this way, two conical regions are formed for the clamping to form a mating shape 15 (not shown), with these regions being spaced apart by a minimum spacing 37 in order to be able to transmit bending moments in the longitudinal axis 9.

Calculations of strength and practical trials have shown that with an arrangement having an elliptical cross-section of the conical body 7 and of its mating shape 15 an optimum utilization of the material takes place when the ellipse is aligned in its plane such that its large axis appears as a perpendicular in a projection towards lateral. In other words, the large axis of the ellipse is aligned in a lateral direction relative to the upper arm (3). Such an arrangement allows a maximum strength to be achieved for the conical clamping connection between the conical body 7 and its mating shape 15 with a width of the shaft 5 limited from anterior to posterior. This applies to arrangements having a full conical body 7 in accordance with FIGS. 2, 5 and 9 as well as to a conical body 7 having a bore 29 in accordance with FIG. 7, as long as the shaft transverse to the longitudinal axis 9 has a lower thickness from posterior to anterior than in other directions.

What is claimed is:

1. A shoulder joint prosthesis having two bearing bodies (1, 2; 11, 12) which slide on one another and which can be respectively connected to an upper arm (3) by a shaft (5) and to a shoulder bone (4) by a platform (6), wherein connection of the prosthesis to the shaft (5) is brought about by a non-rotationally symmetrical, conical body (7) with a self-locking seat, with a periphery (8) of said conical body being form matched to a mating recess (15) in the shaft (5) which is rotationally fixed relative to a longitudinal axis (9) and keyed by an amount of taper so that connection of the prosthesis to the shaft (5) is releasable and repeatedly fixable in a predetermined angular position;

wherein a bearing shell (2) is secured to the platform (6) and a bearing head (1) to the shaft (5);

wherein the bearing head (1) has a spherical recess (19) therein and is connected to the conical body (7) via a fixable ball joint; and wherein a longitudinally slit (21) ball (23) is formed on the conical body (7), the ball having a conical bore (24) with a conical pressure member (25) received in the conical bore (24); and the conical body (7) having a threaded bore (29) adjacent to the conical bore (24) and a screw (27) received in the threaded bore (29) adapted to act on the conical pressure member (25) in order to spread apart the ball (23) and to fix the ball in the spherical recess (19) of the bearing head (1).

2. A shoulder joint prosthesis in accordance with claim 1, wherein the periphery (8) of the conical body (7) and the mating recess (15) are elliptical (10).

3. A shoulder joint prosthesis in accordance with claim 2, wherein the large axis of the elliptical conical body and the mating recess is aligned in a lateral direction relative to the upper arm (3).

4. A shoulder joint prosthesis in accordance with claim 1, wherein the periphery (8) of the conical body (7) and of the mating recess (15) is made as a body having an outline formed by three curves, each curve having a constant diameter (13).

5. A shoulder joint prosthesis in accordance with claim 1, wherein the platform (6) can be fitted with bearing shells (2) of different sizes.

6. A shoulder joint prosthesis in accordance with claim 1, wherein a ball head (11) is secured to the platform (6) and a ball shell (12) is secured to the shaft (5).

7. A shoulder joint prosthesis in accordance with claim 1, wherein the conical body (7) has a depressed central region that defines a pair of raised surfaces adjacent to each side of the depressed central region.

8. A shoulder joint prosthesis in accordance with claim 1, wherein a large axis of the conical body and the mating recess is aligned in a lateral direction relative to the upper arm (3).

9. A shoulder joint prosthesis having two bearing bodies (1, 2; 11, 12) which slide on one another and which can be respectively connected to an upper arm (3) by a shaft (5) and to a shoulder bone (4) by a platform (6), wherein connection of the prosthesis to the shaft (5) is brought about by a non-rotationally symmetrical, conical body (7) with a self-locking seat, with a periphery (8) of said conical body being form matched to a mating recess (15) in the shaft (5) which is rotationally fixed relative to a longitudinal axis (9) and keyed by an amount of taper so that connection of the prosthesis to the shaft (5) is releasable and repeatedly fixable in a predetermined angular position;

wherein a bearing shell (2) is secured to the platform (6) and a bearing head (1) to the shaft (5);

wherein the bearing head (1) has a spherical recess (19) therein and is connected to the conical body (7) via a fixable ball joint; and wherein the conical body (7) has an additional circular cone (17), onto which a spreadable ball body (18) can be placed in a self locking manner, and which circular cone (17) is adapted, when driven into the spreadable ball body (18), to clamp the spreadable ball body (18) in the spherical recess (19) of the bearing head (1).

* * * * *